(12) United States Patent
Klingenbeck et al.

(10) Patent No.: US 10,702,220 B2
(45) Date of Patent: Jul. 7, 2020

(54) TOMOGRAPHY SYSTEM AND METHOD FOR PRODUCING A SERIES OF VOLUME IMAGES OF A VASCULAR SYSTEM

(71) Applicant: Siemens Healthcare GmbH, Erlangen (DE)

(72) Inventors: Klaus Klingenbeck, Aufseß (DE); Markus Kowarschik, Nürnberg (DE); Christopher Rohkohl, Brixen im Thale (AT); Kevin Royalty, Fitchburg, WI (US); Sebastian Schafer, Madison, WI (US)

(73) Assignee: Siemens Healthcare GmbH, Erlangen (DE)

( * ) Notice: Subject to any disclaimer, the term of this patent is extended or adjusted under 35 U.S.C. 154(b) by 82 days.

(21) Appl. No.: 15/780,919

(22) PCT Filed: Dec. 9, 2015

(86) PCT No.: PCT/EP2015/079102
§ 371 (c)(1),
(2) Date: Jun. 1, 2018

(87) PCT Pub. No.: WO2017/092835
PCT Pub. Date: Jun. 8, 2017

(65) Prior Publication Data
US 2018/0368784 A1 Dec. 27, 2018

(30) Foreign Application Priority Data
Dec. 3, 2015 (DE) .................. 10 2015 224 176

(51) Int. Cl.
*A61B 6/03* (2006.01)
*A61B 6/00* (2006.01)
*G06T 11/00* (2006.01)

(52) U.S. Cl.
CPC ............ *A61B 6/032* (2013.01); *A61B 6/4014* (2013.01); *A61B 6/4441* (2013.01); *A61B 6/466* (2013.01);
(Continued)

(58) Field of Classification Search
CPC ....... A61B 6/481; A61B 6/032; A61B 6/4014; A61B 6/4441; A61B 6/504; A61B 6/466;
(Continued)

(56) References Cited

U.S. PATENT DOCUMENTS 5,369,678 A * 11/1994 Chiu .................. A61B 6/06
378/152
6,215,848 B1 4/2001 Linders et al.
(Continued)

FOREIGN PATENT DOCUMENTS

DE 19842474 3/2000
DE 102006040934 3/2008
(Continued)

OTHER PUBLICATIONS

German Office Action for German Application No: 102015224176.9; dated Sep. 6, 2016; 9 pages.
(Continued)

*Primary Examiner* — Brenda C Bernardi
(74) *Attorney, Agent, or Firm* — Lempia Summerfield Katz LLC

(57) ABSTRACT

The invention relates to a tomography system (TA) comprising a first (QD1) and a second (QD2) beam source-detector pair for capturing one series (A1, A2) of projection image data sets (PB1, PB2) each from one projection angle (W1, W2) each and a volume image production system (VE) for producing a series (AV) of volume images (VB) of a vascular system (GS) while taking into account first confidence values (VW1) of the first pixel values (PW1) and/or
(Continued)

while taking into account second confidence values (VW2) of the second pixel values (PW2). The confidence value (VW1, VW2) of a pixel value (PW1, PW2) depends on a pixel-specific traversing length (L) that a projection beam (PS1, PS2) traverses on a path through parts (Gi) of the vascular system (GS) from the first (Q1) or the second (Q2) beam source to a pixel-specific sensor element (S) of the associated first (D1) or second (D2) detector. The invention further relates to a corresponding method (100) for producing a series (AV) of volume images (VB) of a vascular system (GS).

15 Claims, 7 Drawing Sheets

(52) U.S. Cl.
CPC .............. *A61B 6/481* (2013.01); *A61B 6/504* (2013.01); *G06T 11/005* (2013.01); *G06T 11/006* (2013.01); *A61B 6/5205* (2013.01); *A61B 6/5258* (2013.01); *G06T 2211/40* (2013.01)

(58) Field of Classification Search
CPC ... A61B 6/5205; A61B 6/5258; G06T 11/006; G06T 11/005; G06T 2211/40
See application file for complete search history.

(56) References Cited

U.S. PATENT DOCUMENTS

| | | | | |
|---|---|---|---|---|
| 6,377,835 B1* | 4/2002 | Schoenberg | ........... | A61B 5/055 324/306 |
| 6,501,848 B1* | 12/2002 | Carroll | ................. | G06T 11/006 382/128 |
| 6,532,380 B1* | 3/2003 | Close | .................... | A61B 6/481 382/128 |
| 7,519,414 B2 | 4/2009 | Mitschke et al. | | |
| 7,742,629 B2* | 6/2010 | Zarkh | .................... | G06T 7/564 345/419 |
| 8,823,704 B2 | 9/2014 | Mistretta et al. | | |
| 8,957,894 B2 | 2/2015 | Mistretta et al. | | |
| 2005/0226484 A1 | 10/2005 | Basu et al. | | |
| 2006/0139362 A1* | 6/2006 | Lin | ....................... | G06F 3/0425 345/581 |
| 2008/0056438 A1 | 3/2008 | Zellerhoff | | |
| 2009/0016587 A1* | 1/2009 | Strobel | ................... | A61B 6/469 382/130 |
| 2011/0235885 A1* | 9/2011 | Rauch | ................... | A61B 6/4441 382/131 |
| 2013/0237815 A1 | 9/2013 | Klingenbeck | | |
| 2014/0376791 A1 | 12/2014 | Heigl et al. | | |
| 2015/0173699 A1 | 6/2015 | Kyriakou | | |
| 2015/0178585 A1* | 6/2015 | Karafin | ..................... | G06T 5/50 382/197 |
| 2015/0238159 A1* | 8/2015 | Al Assad | ............. | A61B 6/5258 378/5 |
| 2016/0029987 A1* | 2/2016 | Langan | .................. | A61B 6/486 378/8 |
| 2017/0135651 A1* | 5/2017 | Kugler | ................... | A61B 6/032 |

FOREIGN PATENT DOCUMENTS

| | | | |
|---|---|---|---|
| DE | 102012203751 | | 9/2013 |
| DE | 102012217613 | | 3/2014 |
| DE | 102012217613 A1 * | 3/2014 |
| DE | 102013226858 | | 6/2015 |
| DE | 102013203410 | | 5/2016 |

OTHER PUBLICATIONS

Mathematics helps cut dosage in computed tomography, Pressemitteilung: "Mathematics helps cut dosage in computed tomography"; Oct. 4, 2015; 6 pages.
PCT International Search Report and Written Opinion of the International Searching Authority dated Aug. 25, 2016, for corresponding PCT/EP2015/079102.
Victoria Sadick; "Does biplane imaging reduce contrast load, procedural and screening time compared to single-plane imaging in routine diagnostic coronary angiography?"; The Radiographer; 2008; 5 pp.

\* cited by examiner

TOMOGRAPHY SYSTEM AND METHOD FOR PRODUCING A SERIES OF VOLUME IMAGES OF A VASCULAR SYSTEM

CROSS REFERENCE TO RELATED APPLICATIONS

The present patent document is a § 371 nationalization of PCT Application Serial Number PCT/EP2015/079102, filed Dec. 9, 2015 designating the United States, which is hereby incorporated by reference in its entirety. This patent document also claims the benefit of DE 102015224176.9, filed on Dec. 3, 2015, which is also hereby incorporated by reference in its entirety.

FIELD

Embodiments relate to a tomography system.

BACKGROUND

In diagnostics and therapy, ever-increasing demands are made on the performance of medical equipment aimed at avoiding risks to health and physical injury as a consequence of incorrect diagnosis or treatment, as well as to minimize levels of exposure for patients and persons treating them in the application of diagnostic and therapeutic methods.

US 2013/0237815 A1 describes a method for determining a four-dimensional angiography data set by a biplane x-ray device. In the method, two acquisition arrangements that are aligned in different projection directions are used to record a contrast agent in an uptake phase and/or a washout phase in a time-resolved manner, and an animated three-dimensional reconstruction data set is obtained by back-projection. It is proposed to extrapolate or interpolate flow information for those periods of time in which vessel sections are not visible.

U.S. Pat. No. 7,519,414 B2 describes a DSA system for the angiographic visualization of a blood vessel system of a patient from at least two different projection directions. To avoid the need to administer contrast agent via the catheter tip during an endovascular intervention using a microcatheter, a three-dimensional representation of the microcatheter is mixed that has been reconstructed from a plurality of x-ray images and was obtained in a preliminary angiographic examination into a 3D visualization of the blood vessel system. Decoupling the time of the preliminary angiographic examination from the time of the endovascular intervention avoids an application of contrast agent during the therapeutic intervention.

SUMMARY AND DESCRIPTION

The scope of the present invention is defined solely by the appended claims and is not affected to any degree by the statements within this summary. The present embodiments may obviate one or more of the drawbacks or limitations in the related art.

Embodiments provide a tomography system by which a series of volume images may be produced, the volume images of which include a higher imaging fidelity than volume images from series of volume images. The tomography system includes a first and a second beam source-detector pair and a volume image production system for producing a series of volume images of a vascular system.

The first beam source-detector pair is configured for capturing a series of first projection image data sets containing first pixel values from a first projection angle. The second beam source-detector pair is configured for capturing a series of second projection image data sets containing second pixel values from a second projection angle, the second projection angle is different from the first projection angle.

Each of the projection image data sets may be regarded as a data set of a (radiographic) shadow image on which structures located one after another in the beam path produce shadows that overlap one another. The acquisition of one projection image data set each from two different projection angles may (by analogy with quadrature receive methods) be regarded as inphase and quadrature acquisition methods (I&Q acquisition methods) at least when the two projection angles are offset from each other by 90°. A series of volume images refers to a sequence of at least two three-dimensional volume images that succeed one another in time. A first of the at least two three-dimensional volume images shows, for example, an uptake phase and a second of the at least two three-dimensional volume images shows, for example, a washout phase. The tomography system may be, for example, an x-ray tomography system or a fluorescence tomography system.

The beam source and the detector of the first beam source-detector pair may be mounted on a common movable carrier, for example the same C-arm, or on different movable carriers, for example each attached to a separate robot arm. The configuration applies analogously to the beam source and the detector of the second beam source-detector pair. One embodiment provides that both beam source-detector pairs are mounted on a common movable carrier, for example the same C-arm. An image intensifier may be connected to the first and/or the second detector. A separate option provides that the first and/or the second detector includes an image intensifier.

Embodiments further relate to a method for producing a series of volume images of a vascular system, the method including the following: capturing a series of first projection image data sets containing first pixel values from a first projection angle, capturing a series of second projection image data sets containing second pixel values from a second projection angle, the second projection angle is different from the first projection angle, and producing the series of volume images.

Embodiments provide a tomography system including a first beam source-detector pair for capturing a series of first projection image data sets containing first pixel values from a first projection angle, a second beam source-detector pair for capturing a series of second projection image data sets containing second pixel values from a second projection angle, and a volume image production system for producing a series of volume images of a vascular system, the two projection angles is different from each other. The volume image production system is configured for producing the series of volume images of the vascular system taking into account first confidence values of the first pixel values and/or taking into account second confidence values of the second pixel values. The confidence value of a pixel value is in each case dependent on a pixel-specific traversing length that a projection beam traverses on a path through parts of the vascular system from the first or second beam source to a pixel-specific sensor element of the associated first or second detector.

The method for producing a series of volume images of a vascular system includes the following actions. A series of first projection image data sets containing first pixel values is captured from a first projection angle. A series of second projection image data sets containing second pixel values is captured from a second projection angle. The second projection angle is different from the first projection angle. The series of volume images is produced taking into account first confidence values of the first pixel values and/or taking into account second confidence values of the second pixel values, the confidence value of a pixel value is in each case dependent on a pixel-specific traversing length that a projection beam traverses on a path through parts of the vascular system from the first or second beam source to a pixel-specific sensor element of the associated first or second detector.

The series of volume images is produced taking into account first confidence values of the first pixel values and/or taking into account second confidence values of the second pixel values, the confidence value of a pixel value is in each case dependent on a pixel-specific traversing length that a projection beam traverses on a path through parts of the vascular system from the first or second beam source to a pixel-specific sensor element of the associated first or second detector. Each of the measures represent a contribution toward avoiding an artifact (imaging misrepresentation) as a result of incorporating an insufficiently trusted pixel value.

In an embodiment, the volume image production system is configured for forming a weighted average value from pixel values of such first and second pixels the projection beams of which intersect in a voxel, the confidence value of the first pixel value used as a weight of the first pixel value and the confidence value of the second pixel value used as a weight of the second pixel value, to determine a voxel value of the voxel. By incorporating pixel values according to a respective trustedness (e.g. confidence values), each pixel value may contribute according to its trustedness toward (be used for) the calculation of voxel values of such voxels through which a projection beam passes on the way to the pixel-specific sensor element. Pixel values accordingly influence the voxel value of a voxel through which the projection beams pass on a way to the two sensor elements that are assigned to the two pixels in the same way when the two-pixel values are equally trusted (e.g. include an identical confidence value). Furthermore, a pixel value does not influence the voxel value of a voxel through which the projection beam passes on its way to the sensor element that is assigned to the pixel in any fashion when no level of trust at all is attributed to the pixel value (e.g. it has a confidence value of zero). Every intermediate stage between the two extremes may also be taken into account as a result of the confidence-value-dependent weighting of the pixel values (insofar as the quantizations of the confidence values and the pixel values allow for the weighting).

In an embodiment, the volume image production system is configured for replacing a pixel value of a first pixel the projection beam of which intersects the projection beam of a second pixel in a voxel by the second pixel value of the second pixel if the confidence value of the first pixel value falls below a first threshold value to determine a voxel value of the voxel. Alternatively, or in addition, the volume image production system may be configured for replacing a pixel value of a second pixel the projection beam of which intersects the projection beam of a first pixel in the voxel by the first pixel value of the first pixel if the confidence value of the second pixel value falls below the first threshold value. By ignoring such pixel values the confidence values of which fall below the first threshold value it is possible to avoid random anomalies in the volume image that are based on an incorporation of insufficiently trusted pixel values.

In an embodiment, the volume image production system is configured for replacing the pixel value of the first pixel by a temporal interpolation and/or an interpolation between pixel values of pixels that are spatially adjacent to the first pixel if the confidence value of the first pixel value falls below a second threshold value in order to determine a voxel value of a voxel taking into account pixel values of first and second pixels the projection beams of which intersect in the voxel. Alternatively, or in addition, the volume image production system may be configured for replacing the pixel value of the second pixel by a temporal interpolation and/or an interpolation between pixel values of pixels that are spatially adjacent to the second pixel if the confidence value of the second pixel value falls below the second threshold value to determine a voxel value. The temporal and/or spatial interpolation between pixel values of temporally and/or spatially adjacent pixels are configured for pixel values of such pairs of first and second pixels the two-pixel values of which in each case include a confidence value that falls below a predefined threshold value (e.g. the first threshold value).

In an embodiment, the volume image production system is configured for taking an arithmetic average of pixel values of first and second pixels the projection beams of which intersect in a voxel to determine a voxel value of the voxel.

In an embodiment, the tomography system is configured for capturing the series of first and second projection image data sets at a constant first and second projection angle. A mechanical overhead required for a rotation of the two beam source-detector pairs around an orbital axis during the acquisition of the series of projection image data sets may be saved as a result. Furthermore, the volume image production system is simplified if the projection image data sets for the inphase are acquired at a first projection angle that is constant, and the projection image data sets for the quadrature phase are acquired at a second projection angle that is likewise constant.

Alternatively or in addition, the tomography system may be configured for capturing the series of first and second projection image data sets during a synchronous and rotation-angle-offset revolution or partial revolution of the two beam source-detector pairs in a common plane of rotation providing a volume image to be captured simultaneously with the inphase and quadrature acquisitions, though the volume image includes no temporal resolution, or at least not the same temporal resolution as the inphase and quadrature acquisitions.

Alternatively or in addition, the tomography system may be configured for capturing the series of first and second projection image data sets during a synchronous and rotation-angle-offset revolution or partial revolution of the two beam source-detector pairs, that is applicable to both beam source-detector pairs that the respective detector revolves in a plane of rotation that is spaced apart at a distance from the plane of rotation in which the beam source that is assigned to the detector revolves. By spacing apart the plane of rotation of the detector of a beam source-detector pair at a distance from the plane of rotation of the beam source of the beam source-detector pair it is possible that within the reconstructable volume there is no plane in which, from the viewpoint of all voxels of the plane, only at most two of the three Euler angles are varied with the synchronous rotation of the beam source-detector pairs around a common orbital axis. A variation of all three Euler angles for all voxels (with the exception of such voxels through which the orbital axis runs) increases the probability that for at least one of the projection angles the projection beam will pass through few successively disposed vessel sections and consequently the pixel value is particularly significant because the available quantization depth (of, for example, 14 bits) is then used for a minimum of traversed vessel sections.

In an embodiment, the volume image production system is configured for obtaining a first three-dimensional mask image from the projection image data sets of the synchronous and rotation-angle-offset revolution or partial revolution of the two-beam source-detector pairs by removing, from the projection image data sets or the volume image data reconstructed therefrom, such data that changes during the revolution or partial revolution of the two beam source-detector pairs avoiding the need to factor in additional time and an exposure of the patient for a separate mask run.

In an embodiment, the volume image production system is configured for obtaining the series of volume images of the vascular system taking into account a second three-dimensional mask image from a mask run. The configuration provides for a visualization of details that are irrelevant to an examination and/or treatment task that is to be performed with the tomography system to be avoided in the volume images. Because the tomography system is configured for performing the mask run, the need to provide a further tomography system for a separate preparatory examination for producing the mask image is avoided. Furthermore, the reliability and/or quality of the mask image registration are/is enhanced if both the mask image and the projection image data sets of the fill phases and/or washout phases are produced using the same tomography system.

Alternatively, or in addition, the tomography system may be configured for obtaining the series of volume images of the vascular system taking into account a third three-dimensional mask image that is obtained from an external data source. The configuration provides for the mask image to be produced in a separate preparatory examination by a further tomography system and transferred to the tomography system for registration on the volume images for the fill phase and/or washout phase. The embodiment may considerably simplify the tomography system because, for the capturing of the projection image data sets from the two projection angles and for producing the series of volume images of a vascular system, the tomography systems needs to be neither mechanically nor electrically so complicated in structure as a biplane tomography system for producing a three-dimensional mask image. For example, a rotation of the two acquisition arrangements (around an orbital axis) is not necessary for the inphase and quadrature acquisition method during the fill phase and/or during the washout phase. Conversely, a monoplane tomography system is sufficient for producing a three-dimensional mask image.

A beneficial development provides that the volume image production system is configured for using the first and/or the second and/or the third three-dimensional mask image of the vascular system as a boundary image for the series of volume images. The configuration provides for the volume images produced by the volume image production system to be kept free of content that is of no interest for an examination and/or treatment that is to be performed by the tomography system by restricting the content of the volume images to a visualization of fill states of parts of the vascular system.

In an embodiment, the second projection angle is offset by 90° from the first projection angle. As a result, the second beam source-detector pair is used in the best possible way for performing the inphase and quadrature acquisition method.

The phrase 'configured for' is used in the present context to define a functional characteristic of the tomography system. An assessment whether the tomography system possesses the functional characteristic claimed in each case may require the tomography system to be commissioned in accordance with the applicable specifications. The possibility of upgrading software in a computer-controlled tomography system by subsequently loading a more advanced piece of software so that the computer-controlled tomography system may have the claimed functional characteristic is in the context not regarded as such a functional characteristic for which the specific tomography system is configured. In other words, a tomography system may be deemed as configured for the functional characteristic only when a realization of the functional characteristic exists not just in principle, but the realization of the functional characteristic is demonstrably turned into reality by a developer, manufacturer, importer, provider or operator. In order to judge whether such a realization of the functional characteristic is present, a user guide, a tender document or a service or development document of the tomography system may also be used provided it has been verified or may be assumed that the document used for that purpose fittingly describes the actual structure and/or the actual functional characteristics of the tomography system.

DETAILED DESCRIPTION

Figure 1:
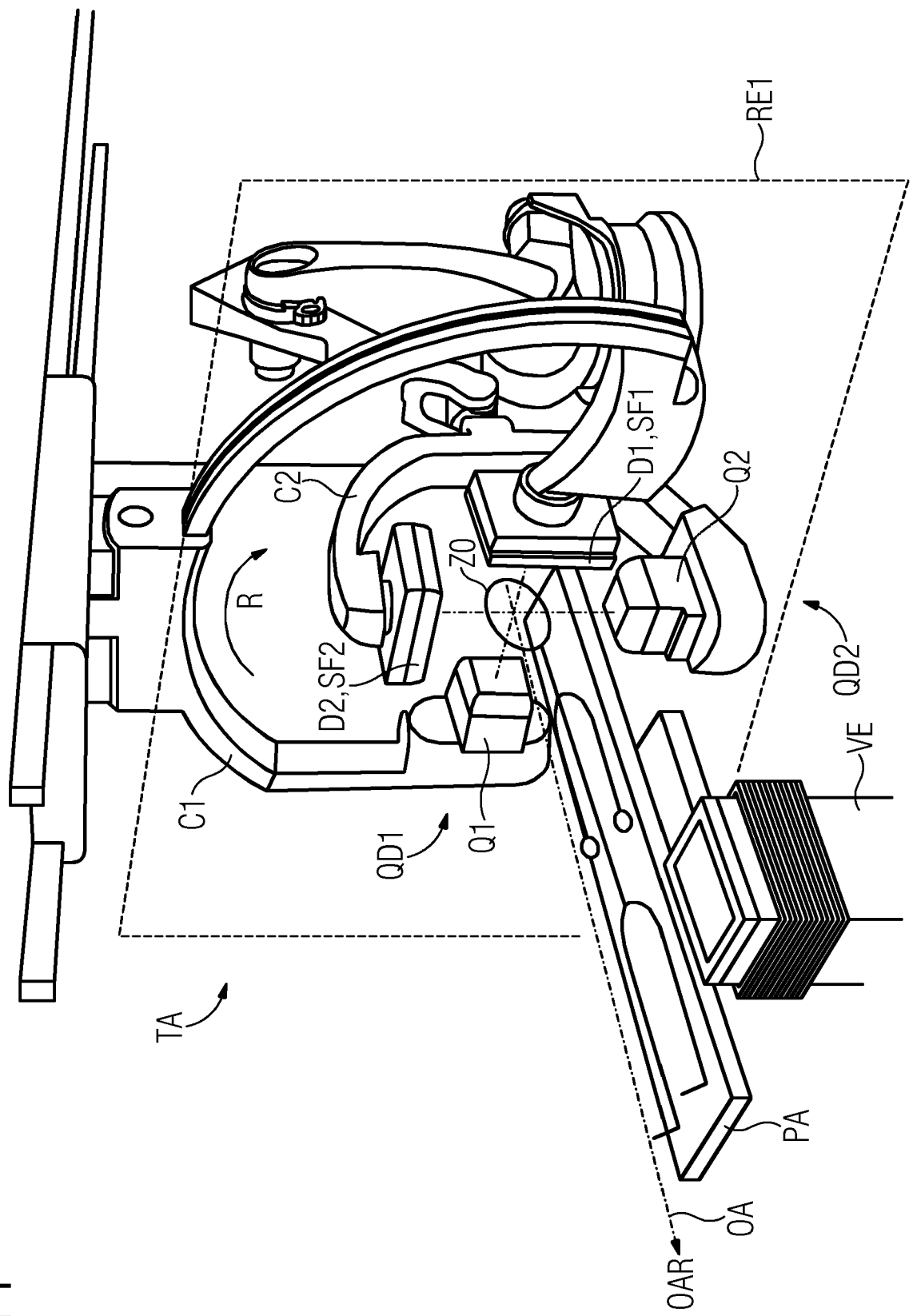
FIG. 1 depicts a schematic perspective view of a biplane tomography apparatus according to an embodiment including a patient support platform and two C-arms, each of which has a beam source-detector pair.

The biplane tomography system TA depicted in FIG. 1 includes a first C1 and a second C2 C-arm as well as a patient support platform PA and a volume image production system VE. A first beam source Q1 and a first detector D1 are mounted on the first C-arm C1. A second beam source Q2 and a second detector D2 are mounted on the second C-arm C2. Each of the two detectors D1, D2 includes a sensor surface SF1 and SF2, respectively.

Figure 2:
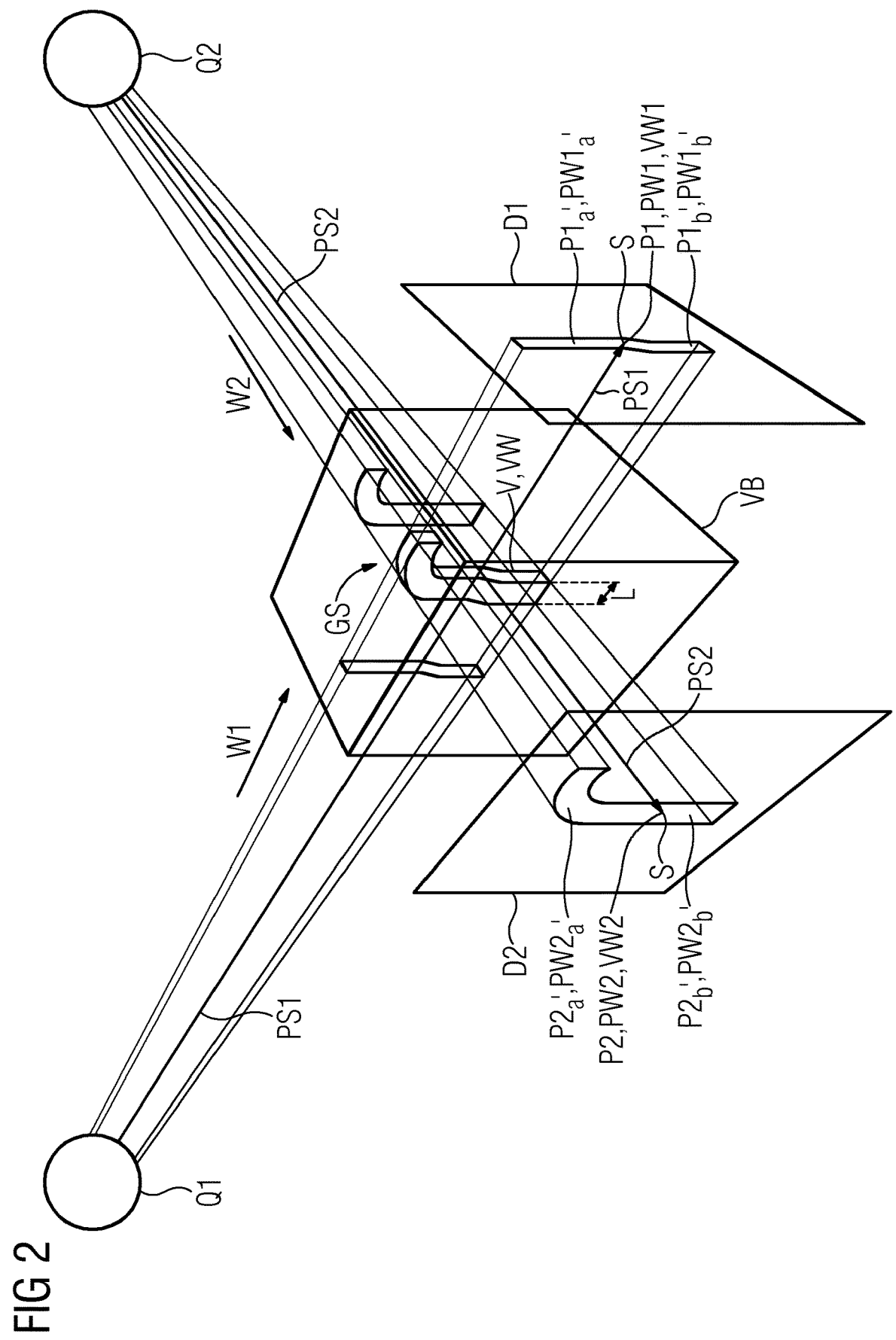
FIG. 2 depicts a schematic perspective view of beam paths of a biplane tomography apparatus in an inphase and quadrature arrangement according to an embodiment.

The first beam source-detector pair QD1 is configured for capturing a series A1 of first projection image data sets PB1 containing first pixel values PW1 from a first projection angle W1, and a second beam source-detector pair QD1 is configured for capturing a series A2 of second projection image data sets PB2 containing second pixel values PW2 from a second projection angle W2, the two projection angles W1, W2 are different from each other (see FIG. 2).

The volume image production system VE is configured for producing the series AV (see FIG. 3) of volume images VB of the vascular system GS taking into account first confidence values VW1 of the first pixel values PW1 and/or taking into account second confidence values VW2 of the second pixel values PW2. The confidence value VW1 of a first pixel value PW1 is dependent on a pixel-specific traversing length L (see FIG. 2) that a first projection beam PS1 traverses on a path through parts Gi of the vascular system GS from the first beam source Q1 to a pixel-specific sensor element S of the associated first detector D1. Similarly, the confidence value VW2 of a second pixel value PW2 is dependent on a pixel-specific traversing length L that a second projection beam PS2 traverses on a path through parts Gi of the vascular system GS from the second beam source Q2 to a pixel-specific sensor element S of the associated second detector D2.

In an embodiment, the volume image production system VE is configured for forming a weighted average value from pixel values of such first P1 and second P2 pixels the projection beams PS1, PS2 of which intersect in a voxel V in order to determine a voxel value VW of the voxel V, the confidence value VW1 of the first pixel value PW1 used as a weight of the first pixel value PW1 and the confidence value VW1 of the second pixel value PW2 used as a weight of the second pixel value PW2. By incorporating pixel values PW1, PW2 according to a respective trustedness (e.g. the confidence values), each pixel value PW1, PW2 may contribute according to its trustedness toward (be used for) the calculation of voxel values VW of such voxels V through which a projection beam PS1, PS2 passes on its way to the pixel-specific sensor element S. Pixel values PW1, PW2 accordingly influence the voxel value VW of a voxel V through which the projection beams PS1, PS2 pass on the way to the two sensor elements S that are assigned to the two pixels P1, P2 in the same way when the two pixel values PW1, PW2 are equally trusted (e.g. include an identical confidence value VW1, VW2). Furthermore, a pixel value PW1, PW2 does not influence the voxel value of a voxel V through which the projection beam PS1, PS2 passes on its way to the sensor element S that is assigned to the pixel P1, P2 in any fashion when no level of trust at all is attributed to the pixel value PW1, PW2 (i.e. it has a confidence value of zero). Every intermediate stage between the two extremes is also taken into account as a result of the confidence-value-dependent weighting of the pixel values PW1, PW2 (insofar as the quantizations of the confidence values VW1, VW2 and the quantizations of the pixel values PW1, PW2 allow for this).

In an embodiment, the volume image production system VE is configured for replacing a pixel value PW1 of a first pixel P1 the projection beam PS1 of which intersects with the projection beam PS2 of a second pixel P2 in a voxel V by the second pixel value PW2 of the second pixel P2 in order to determine a voxel value VW of the voxel V if the confidence value VW1 of the first pixel value PW1 falls below a first threshold value. Alternatively, or in addition, the volume image production system VE may be configured for replacing a pixel value PW2 of a second pixel P2 the projection beam PS2 of which intersects with the projection beam PS1 of a first pixel P1 in the voxel V by the first pixel value PW1 of the first pixel P1 if the confidence value VW2 of the second pixel value PW2 falls below the first threshold value. By ignoring such pixel values PW1, PW2 the confidence value VW1, VW2 of which falls below the first threshold value it is possible to avoid random anomalies in the volume image VB that are based on an incorporation of insufficiently trusted pixel values PW1, PW2.

FIG. 2 depicts an arrangement for acquiring a first series A1 of first projection image data sets PB1 and synchronously acquiring a second series A2 of second projection image data sets PB2, a second projection direction W2 for acquiring the second projection image data sets PB2 arranged perpendicularly to a first projection direction W1 for acquiring the first projection image data sets PB1.

Figure 3:
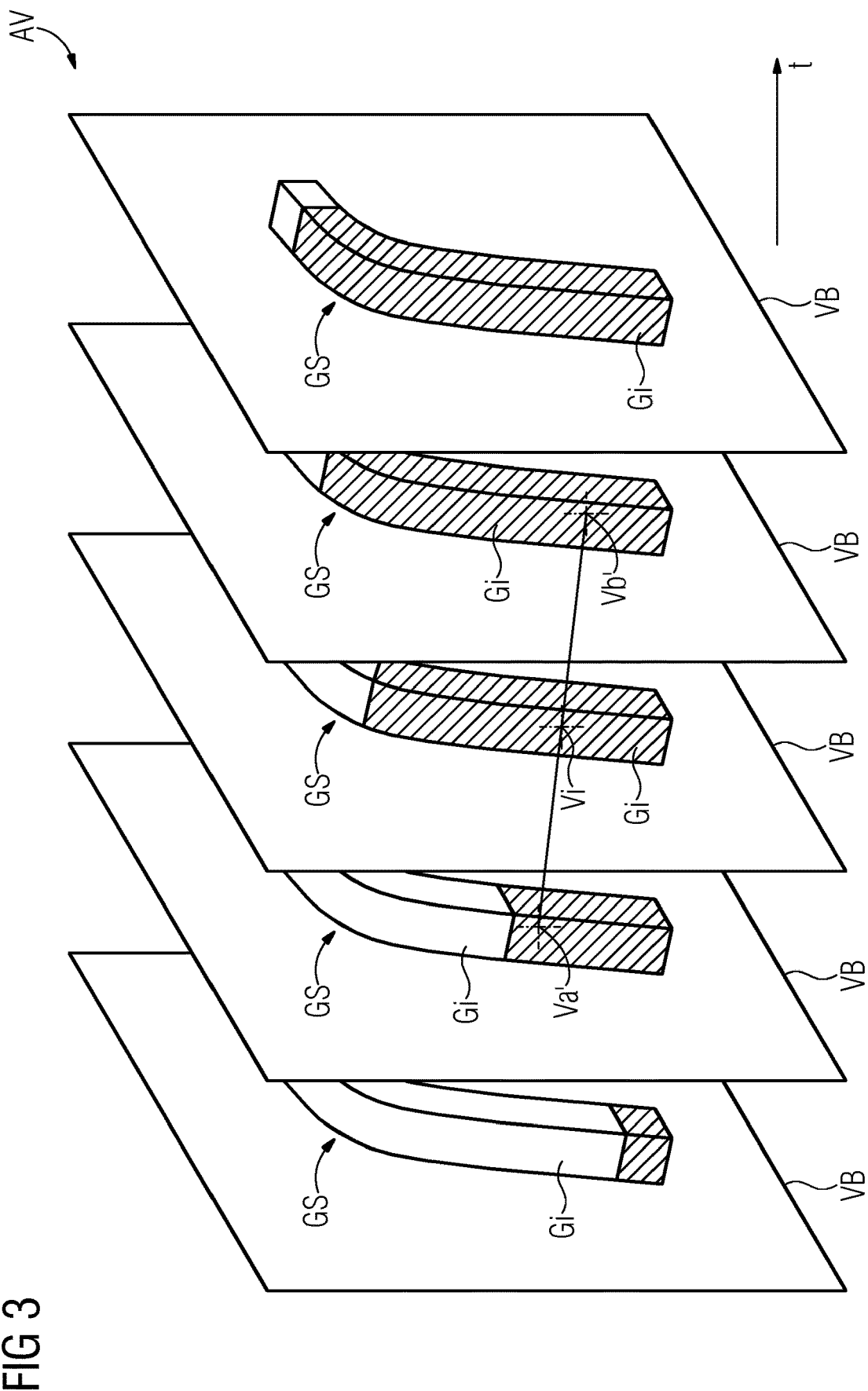
FIG. 3 depicts a schematic perspective view of a series of volume images plotted along a time axis according to an embodiment.

FIG. 3 depicts a series AV of volume images VB including different fill states of a vascular system GS over the time axis t (the hatching indicates the respective extent of the filling).

In an embodiment, the volume image production system is configured for replacing the pixel value PW1 of the first pixel P1 by a temporal interpolation and/or an interpolation between pixel values PW1' of pixels P1' that are spatially adjacent to the first pixel P1 if the confidence value VW1 of the first pixel value P1 falls below a second threshold value (see also FIG. 2) to determine a voxel value VW of a voxel V taking into account pixel values PW1, PW2 of first P1 and second P2 pixels the projection beams PS1, PS2 of which intersect in the voxel V. An interpolation may be performed only using such pixel values PW' the confidence value of which does not fall below the second threshold value.

Alternatively, or in addition, the volume image production system VE may be configured for replacing the pixel value PW2 of the second pixel P2 by a temporal interpolation and/or an interpolation between pixel values PW2' of pixels P2' that are spatially adjacent to the second pixel P2 in order to determine a voxel value VW if the confidence value VW2 of the second pixel value PW2 falls below the second threshold value. An interpolation may be performed only using such pixel values PW' the confidence value of which does not fall below the second threshold value.

FIG. 3 depicts a voxel Vi to be interpolated that lies at the point of intersection of the projection beams PS1, PS2 of the pixels P1, P2 (see FIG. 2). Correspondingly, a first temporally and spatially adjacent voxel Va' lies at the point of intersection of projection beams of the pixels P1a', P2a' and a second spatially adjacent voxel Vb' lies at the point of intersection of projection beams of the pixels P1b', P2b'. The voxel Vb' is a first of two voxels Va', Vb' that are temporally and spatially adjacent to the voxel Vi to be interpolated. The voxel Vb' is a second of two voxels Va', Vb' that are temporally and spatially adjacent to the voxel Vi to be interpolated. The connecting line between the two temporally and spatially adjacent voxels Va' and Vb' is a straight interpolation line between the neighbor voxels Va', Vb' the confidence values of which in each case do not fall below the second threshold value.

The temporal and spatial interpolation between pixel values of temporally and/or spatially adjacent pixels may be configured for pixel values PW1, PW2 of such pairs of first P1 and second pixels P2 the two-pixel values PW1, PW2 of which include a confidence value VW1, VW2, respectively, that falls below a predefined threshold value (for example the first threshold value).

In an embodiment, the volume image production system VE is configured for taking an arithmetic average of pixel values PW1, PW2 of first P1 and second P2 pixels the projection beams PS1, PS2 of which intersect in a voxel V in order to determine a voxel value VW of the voxel V.

In an embodiment, the volume image production system VE is configured for determining a first three-dimensional mask image M1 from the projection image data sets PB1, PB2 of the synchronous and rotation-angle-offset revolution or partial revolution of the two-beam source-detector pairs QD1, QD2. To that end, the volume image production system VE removes from the projection image data sets PB1 or the volume image data reconstructed therefrom such data that changes during the revolution or partial revolution of the two-beam source-detector pairs QD1, QD2 (i.e. for example that is dependent on the fill state or washout state of the vascular system). For the embodiment, the synchronous and rotation-angle-offset revolution or partial revolution of the two-beam source-detector pairs QD1, QD2 extends at least over a complete fill phase or at least over a complete washout phase (during which the series A1, A2 of projection image data sets PB1, PB2 are captured, for example at a clock rate of 15 or 30 images per second). The concept of obtaining a three-dimensional mask image M1 during a fill phase or during a washout phase may also be realized using a monoplane tomography system that has just one beam source-detector pair QD1.

Alternatively, or in addition, the tomography system TA may be configured for obtaining the series AV of volume images VB of the vascular system GS from a mask run ML, taking into account a second three-dimensional mask image M2. The configuration provides a visualization of details (of parts of a skull, for example) that are of no relevance to an examination and/or treatment task that is to be performed with the tomography system TA to be avoided in the volume images VB. Because the tomography system TA is configured for performing the mask run ML, the need to provide a further tomography system TA for a separate preparatory examination for producing the mask image is avoided. Furthermore, the reliability and/or quality of the registration of the mask image are/is enhanced if both the mask image and the projection image data sets PB1, PB2 are produced by the same tomography system TA during fill phases and/or washout phases.

Figure 4:
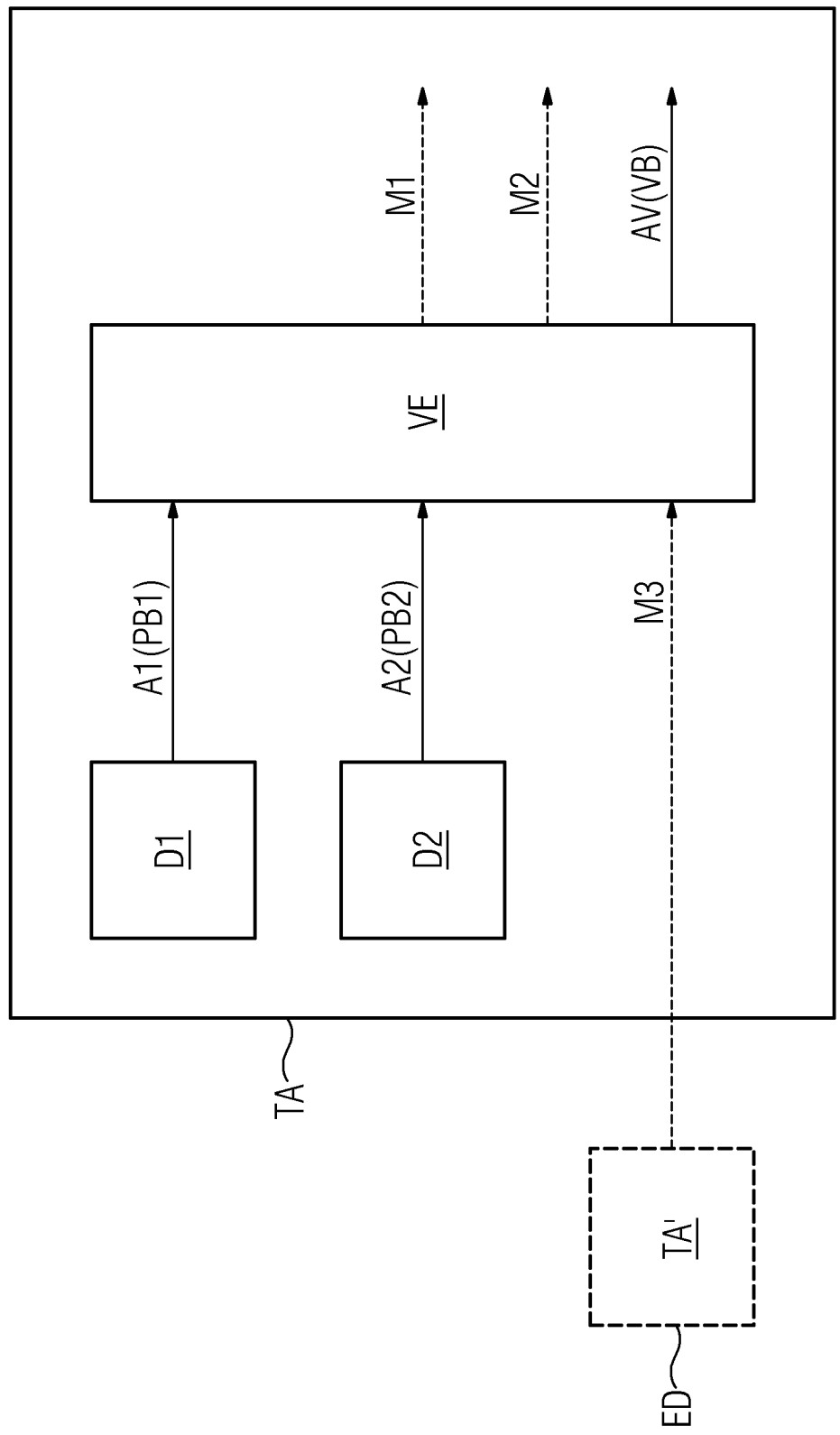
FIG. 4 depicts an overview of a data flow between a tomography system according to an embodiment.

As FIG. 4 depicts, the tomography system TA may alternatively or additionally be configured for obtaining the series AV of volume images VB of the vascular system GS taking into account a third three-dimensional mask image M3 obtained from an external data source ED. The configuration provides the mask image M3 to be produced by a further tomography system TA' in a separate preparatory examination and transferred to the tomography system TA for registration on the volume images VB for the fill phase and/or washout phase. The embodiment may considerably simplify the tomography system TA because, for the capturing of the projection image data sets PB1, PB2 from the two projection angles W1, W2 and for producing the series AV of volume images VB of a vascular system GS, it does not need to be constructed either mechanically or electrically in so complex a manner as a biplane tomography system for producing a three-dimensional mask image. A rotation R of the two acquisition arrangements QD1, QD2 (around an orbital axis OA) is not necessary for the inphase and quadrature acquisition method (during the fill phase and/or the washout phase). Conversely, a monoplane tomography system TA' is adequate for producing a three-dimensional mask image M3.

Embodiments provide that the volume image production system VE is configured for using the first M1 and/or the second M2 and/or the third M3 three-dimensional mask image of the vascular system GS as a boundary image for the series AV of volume images VB. The configuration provides the volume images VB produced by the volume image production system VE to be kept free of content that is of no interest for an examination and/or treatment that is to be performed by the tomography system TA in that the content of the volume images VB is restricted to a visualization of fill states of parts Gi of the vascular system GS.

The second projection angle W2 may be offset by 90° from the first projection angle W1. As a result, the second beam source-detector pair QD2 is used in the best possible way for performing the inphase and quadrature acquisition method.

The tomography system TA may be configured for capturing the series A1, A2 of the first PB1 and second PB2 projection image data sets at a constant first W1 and a constant second W2 projection angle. A mechanical overhead required for a rotation R of the two-beam source-detector pairs QD1, QD2 around an orbital axis OA during the capturing of the series A1, A2 of projection image data sets PB1, PB2 may be saved as a result. Furthermore, the volume image production system VE is simplified if the first projection image data sets PB1 for the inphase are acquired at a first projection angle W1 that is constant, and the second projection image data sets PB2 for the quadrature phase are acquired at a second projection angle W2 that is likewise constant.

Alternatively, or in addition, the tomography system TA may be configured for capturing the series A1, A2 of the first PB1 and second PB2 projection image data sets during a synchronous and rotation-angle-offset revolution or partial revolution of the two beam source-detector pairs QD1, QD2 in a common plane of rotation RE1. The configuration provides a volume image VB to be captured simultaneously with the inphase and quadrature acquisitions PB1, PB2, though the volume image VB has no temporal resolution or at least not the same temporal resolution as the inphase and quadrature acquisitions PB1, PB2.

Figure 5:
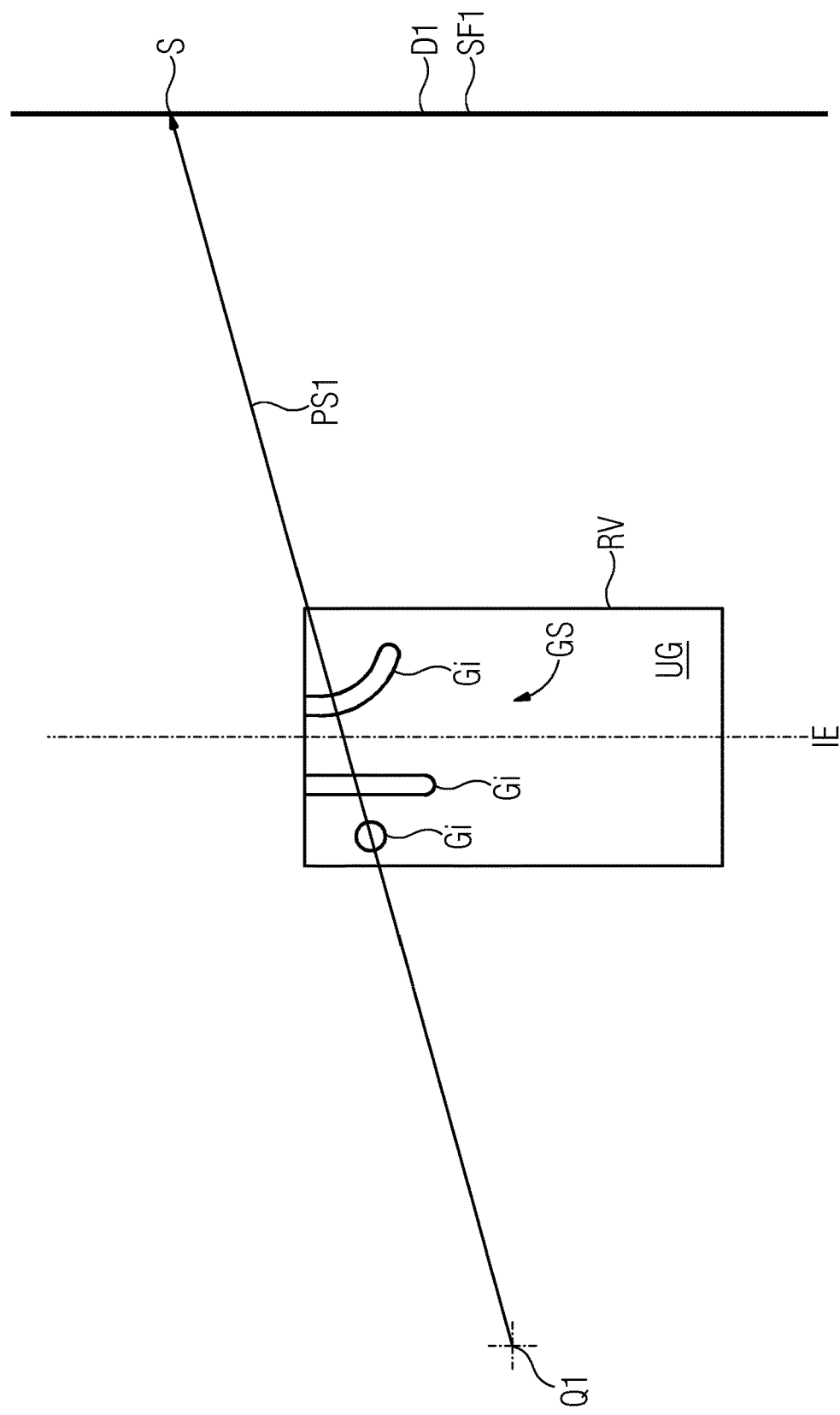
FIG. 5 depicts a schematic representation of a course of a projection beam that passes through a plurality of successive vessel sections of a vascular system according to an embodiment.

FIG. 5 depicts the problem of overlapping shadow images of vessels Gi of a vascular system GS when determining a volume image VB from a reconstructable volume RV of an object ZO that is to be examined. The dash-dotted line depicts the location of an isoplane IE. A first projection beam PS1 may traverse several vessels Gi (without loss of generality, three vessels are depicted). When passing through each of the vessels Gi, the projection beam PS1 is attenuated (due to absorption and possibly also scattering). The attenuation of the intensity of the projection beam PS1 is dependent both on the composition of the respective tissue Gi and on a respective traversing length of the projection beam PS1 through the respective vessel Gi. Furthermore, the intensity of the projection beam PS1 is also attenuated in the course of its passage through surrounding tissue UG that envelops the vessels Gi traversed by the projection beam PS1.

In the volume image VB that the volume image production system VE has to determine, there is contained, for each vessel Gi is traversed by the projection beam PS1, information indicating how greatly the vessel Gi is traversed contributes toward the attenuation of the intensity of the projection beam PS1. The strength of the attenuation may be interpreted as a grayscale value. If the attenuation of the intensity of the projection beam PS1 through each individual vessel Gi and the surrounding tissue UG is numbered in each case with a linear attenuation measure, the overall attenuation of the intensity of the projection beam PS1 is calculated from the product of the intensity attenuations of the individual vessels Gi and of the surrounding tissue UG. An overall attenuation of the intensity of the projection beam PS1 may be calculated from the sum of attenuations of the individual vessels Gi and of the surrounding tissue UG if the attenuations or the overall attenuation are in each case a logarithm of the linear attenuation measure. The resolution capacity in terms of the overall attenuation (e.g. the so-called grayscale number) is limited by a usable bit depth of the analog-to-digital converters of the detector (where the usable bit depth may additionally be limited also by interference effects such as quantum noise).

For example, at a bit depth of 12 bits (4096 intensity values) it is possible to resolve a maximum of 6 vessel sections with a discretization of 4 attenuation values (2 bits) or a maximum of 4 vessel sections with a discretization of 8 attenuation values (3 bits).

Each voxel V may be passed through by projection beams from as many directions as possible in order also in one instance to use a beam direction (line of sight through the "tangled skein" of the vascular system) in which not too many vessel sections Gi are located so that the few vessel sections or only vessel section Gi in the beam direction are/is captured in isolation with the highest possible dynamics (bit depth).

The aim of passing projection beams through each voxel V from as many directions as possible is missed for the voxels V of the plane of rotation RE1, because although the voxels V of the plane of rotation RE1 are traversed from different circumferential angles, the voxels V are only passed through exclusively in the radial direction. Of the Euler angles, only the roll angle is then varied. In the case of all other voxels V (that are not located in the plane of rotation), the rotation R also leads to a voxel-specific variation of yaw angle and pitch angle.

Figure 6:
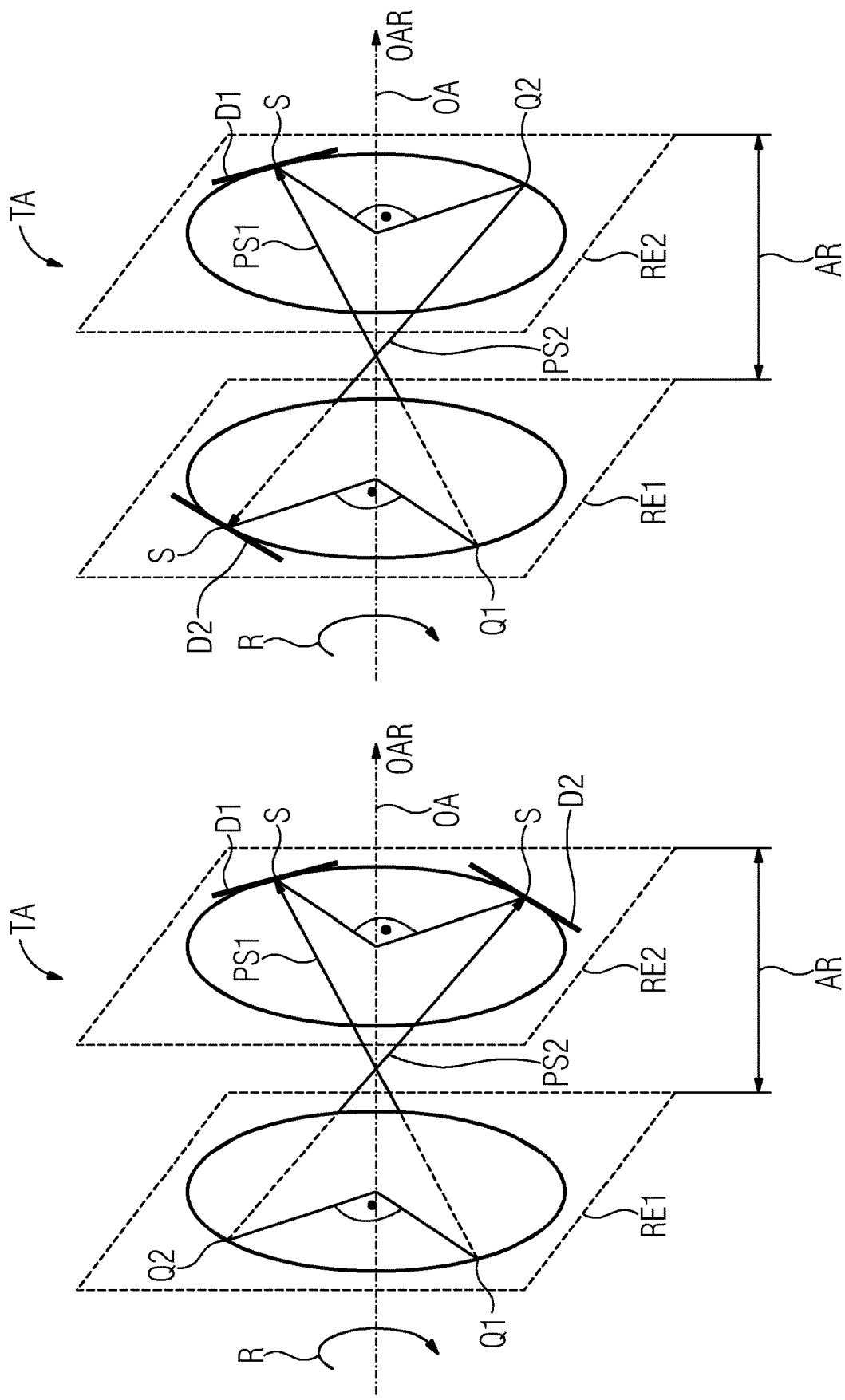
FIG. 6 depicts a schematic perspective view of beam paths of two embodiments of a biplane tomography apparatus having two planes of rotation that are spaced apart at a distance from each other.

FIG. 6 schematically depicts two embodiment variants of a tomography system TA that mitigates the overlapping problem by an arrangement in which the planes of rotation RE1, RE2 of beam source Q1, Q2 and detector D1, D2 are spaced apart from each other. With an adequate separating distance AR of the planes of rotation RE1, RE2 (and alignment of the central beam onto the respective detector D1, D2 in the other plane of rotation) it is possible, for each considered voxel V, to compel the beam direction to reel through the considered voxel V (i.e. it does not remain in the same plane).

The concept for reducing the overlapping problem may also be realized by a monoplane tomography system including only one beam source Q1 and only one detector D1. The system may for example be the tomography system TA' with which the mask run ML is performed. Optionally, the concept may be combined with the previously described concept in which the volume image production system VE is configured for determining the three-dimensional mask image M1 from the projection image data sets PB1 of a revolution or partial revolution of the beam source-detector pair QD1. The volume image production system VE removes, from the projection image data sets PB1 or the volume image data reconstructed therefrom, such data that changes during the revolution or partial revolution of the two-beam source-detector pairs QD1, QD2 (e.g. removes such data, for example, that is dependent on the fill state or washout state of the vascular system GS).

In an embodiment depicted in the schematic on the left in FIG. 6, the second beam source Q2 revolves in the first plane of rotation RE1 and the second detector D2 revolves synchronously in a second plane of rotation RE2 that is spaced apart at a distance from the first plane of rotation RE1. In the embodiment variant shown in the schematic on the right in FIG. 6, the second beam source Q2 revolves in the second plane of rotation RE2 and the second detector D2 revolves synchronously in the first plane of rotation RE1.

By spacing apart the plane of rotation RE1 of the beam source Q1 of the first beam source-detector pair QD1 at a distance from the plane of rotation RE2 of the detector D1 of the first beam source-detector pair QD1, and by the corresponding measure for the second beam source-detector pair QD2, it is provided that within the reconstructable volume RV there is no plane in which, from the viewpoint of any voxel V of the plane, only at most two of the three Euler angles are varied with the synchronous rotation R of the beam source-detector pairs QD1, QD2 around the common orbital axis OA. A variation of all three Euler angles for all voxels V (with the exception of such voxels through which the orbital axis runs) promotes a probability that, during the revolution or partial revolution, the projection beam PS1, PS2 for at least one of the acquisition angles passes through particularly few successively disposed vessel sections Gi and consequently the pixel value PW1, PW2 of the projection beam PS1, PS2 is significant, because then the available quantization depth (of, for example, 14 bits) is used for determining the attenuation of an intensity of the projection beam PS1 caused by vessel sections Gi for a minimum of traversed vessel sections Gi.

The first C-arm C1 may, for example, perform an angular rotation around an orbital axis OA, while the second C-arm C2 performs an orbital rotation R around the same orbital axis OA. During the orbital rotation R of the second C-arm C2, the (notional) plane in which the second C-arm C2 is located remains unchanged. During the angular rotation R of the first C-arm C1, the first C-arm C1 revolves around a mounting axis BA1 of the C-arm. A synchronous scan may also be performed in which the C-arms C1, C2 are arranged prior to the scan in such a way that during the scan both C-arms C1, C2 perform an angular rotation R or that prior to the scan the C-arms C1, C2 are arranged in such a way that during the scan both C-arms C1, C2 perform an orbital rotation R.

The tomography system TA may be configured for applying an iterative reconstruction method, for example, a model-based iterative reconstruction method, to reconstruct a volume image VB of the series AV of volume images VB or the mask image M1, M2. The configuration provides (in comparison with other reconstruction methods) a radiation dose to be reduced while retaining the same image quality or the image quality to be increased while maintaining an unchanged radiation dose in that a noise component and/or a proportion of artifacts are/is reduced and/or a low-contrast detectability is improved.

Imaging iterative reconstruction methods may be known. The phrase 'iterative reconstruction methods' serves to denote convergent, numeric solution methods in which a two- or three-dimensional image (e.g. the three-dimensional volume image VB) of the irradiated object ZO is estimated in each iteration step. The estimated images of the individual iteration steps are estimated through comparison between projection image data sets obtained by a simulation of a forward projection with the estimate (e.g. imaging through the estimated three-dimensional volume image) from the preceding iteration step in each case, and actually captured projection image data sets. The forward projection is simulated under those irradiation conditions under which the projection image data sets (projection images) were acquired. After several preceding iteration steps, the estimate of the three-dimensional volume image VB of the irradiated object ZO is so good that a simulated forward projection diverges only marginally from the actually acquired projection image data sets (projection images) and consequently the estimated three-dimensional volume image VB replicates the real object to be examined very well. A prerequisite is a convergence of the chosen estimation method. By a model-based iterative reconstruction method is understood an iterative reconstruction method that simulates forward projections more closely to reality by taking into account additional operating parameters (for example, beam width, angular straggling) and/or inherently unwanted physical effects (for example, beam hardening).

Figure 7:
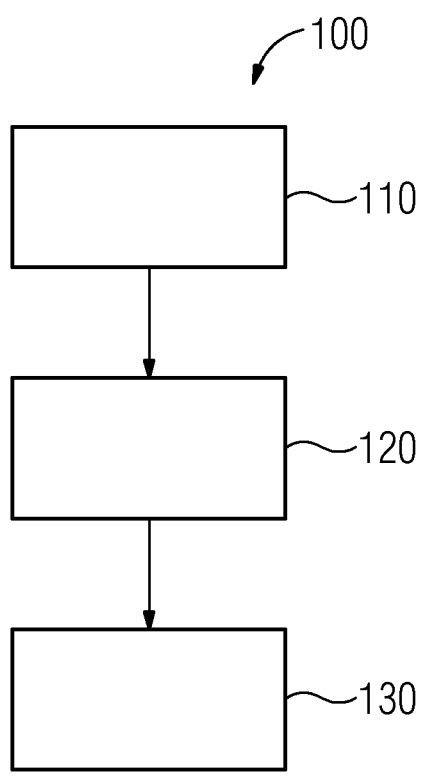
FIG. 7 depicts an execution sequence of a method for producing a series of volume images of a vascular system according to an embodiment.

The method 100 depicted in FIG. 7 for producing a series AV of volume images VB of a vascular system GS includes the following actions. In a first action 110, a series A1 of first projection image data sets PB1 containing first pixel values PW1 is captured from a first projection angle W1. In a second action 120, a series A2 of second projection image data sets PB1 containing second pixel values PW2 is captured from a second projection angle W2, the second projection angle W2 different from the first projection angle W1. In a third action 130, the series AV of volume images VB is produced taking into account first confidence values VW1 of the first pixel values PW1 and/or taking into account second confidence values VW2 of the second pixel values PW2, the confidence value VW1, VW2 of a pixel value PW1, PW2 are dependent in each case on a pixel-specific traversing length L that a projection beam P1, P2 traverses on a path through parts Gi of the vascular system GS from the first Q1 or second Q2 beam source to a pixel-specific sensor element S of the associated first D1 or second D2 detector.

Embodiments further relate to a tomography system TA including the following: a first QD1 and a second QD2 beam source-detector pair for capturing a respective series A1, A2 of projection image data sets PB1, PB2 from a respective projection angle W1, W2, as well as to a volume image production system VE for producing a series AV of volume images VB of a vascular system GS taking into account first confidence values VW1 of the first pixel values PW1 and/or taking into account second confidence values VW2 of the second pixel values PW2. The confidence value VW1, VW2 of a pixel value PW1, PW2 is dependent in each case on a pixel-specific traversing length L that a projection beam PS1, PS2 traverses on a path through parts Gi of the vascular system GS from the first Q1 or second Q2 beam source to a pixel-specific sensor element S of the associated first D1 or second D2 detector.

Embodiments take into account pixel-specific confidence values VW1, VW2 that are dependent on a respective pixel-specific traversing length L that a pixel-specific projection beam PS1, PS2 traverses on a path through parts Gi of the vascular system GS to the pixel-specific sensor element S.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A tomography system comprising:
    a first beam source-detector pair configured to capture a series of first projection image data sets containing first pixel values from a first projection angle;
    a second beam source-detector pair configured to capture a series of second projection image data sets containing second pixel values from a second projection angle, wherein the two projection angles are different from each other; and
    a volume image production system configured to determine voxel values for a series of volume images of a vascular system by calculating a weighted average value for a respective voxel from pixel values of first- and second-pixels values of the projection beams that intersect in the respective voxel;
    wherein a confidence value of a first pixel value is used as a weight of the first pixel value and a confidence value of a second pixel value is used as a weight of the second pixel value to calculate the weighted average value;
    wherein the confidence values are determined as a function of a length of the vascular system that is traversed by a respective projection beam from a respective beam source through a respective pixel to the respective detector.

2. The tomography system of claim 1, wherein the volume image production system is configured to replace a pixel value of a first pixel that includes a projection beam that intersects in a voxel with the projection beam of a second pixel by a second pixel value of the second pixel when the confidence value of the first pixel value falls below a first threshold value in order to determine a voxel value of the voxel or the volume image production system is configured to replace the pixel value of the second pixel that includes a projection beam that intersects in the voxel with the projection beam of the first pixel by the first pixel value of the first pixel when the confidence value of the second pixel value falls below the first threshold value.

3. The tomography system of claim 1, wherein the volume image production system is configured to replace a pixel value of a first pixel by a temporal interpolation, an interpolation, or the temporal interpolation and the interpolation between pixel values of pixels that are spatially adjacent to the first pixel when the confidence value of the first pixel value falls below a second threshold value in order to determine a voxel value of a voxel taking into account pixel values of first pixels and second pixels with projection beams that intersect in the voxel or the volume image production system is configured to replace a pixel value of a second pixel by a temporal interpolation, an interpolation, or the temporal interpolation and the interpolation between pixel values of pixels that are spatially adjacent to the second pixel when the confidence value of the second pixel value falls below the second threshold value.

4. The tomography system of claim 1, wherein the tomography system is configured to capture the series of first projection image data sets and the series of second projection image data sets at a constant first projection angle and a second projection angle, or is configured to capture the series of first projection image data sets and the series of second projection image data sets during a synchronous and rotation-angle-offset revolution or partial revolution of the first beam source-detector pair and the second beam source-detector pair in a common plane of rotation or during a synchronous and rotation-angle-offset revolution or partial revolution of the two beam source-detector pairs, wherein a respective detector of the first beam source-detector pair and the second beam source-detector pair revolves in a plane of rotation that is spaced apart at a distance from the plane of rotation in which the beam source that is assigned to the respective detector revolves.

5. The tomography system of claim 1, wherein the volume image production system is configured to obtain a first three-dimensional mask image from the first projection image data set and the second projection image data set of a synchronous and rotation-angle-offset revolution or partial revolution of the first beam source-detector pair and the second beam source-detector pair by removing, from the first projection image data set and the second projection image data set or the series of volume images reconstructed therefrom, such data that changes during the revolution or partial revolution of the first beam source-detector pair and the second beam source-detector pair.

6. The tomography system of claim 5, wherein the volume image production system is configured to obtain the series of volume images of the vascular system taking into account a second three-dimensional mask image from a mask run, a third three-dimensional mask image that is obtained from an external data source, or the second three-dimensional mask image and the third three-dimensional mask image.

7. The tomography system of claim 6, wherein the volume image production system is further configured to use at least one of the first three-dimensional mask image, the second three-dimensional mask image, or the third three-dimensional mask image as a boundary image for the series of volume images.

8. The tomography system of claim 1, wherein the second projection angle is offset by 90° from the first projection angle.

9. A method for producing a series of volume images of a vascular system, the method comprising:
capturing a series of first projection image data sets containing first pixel values from a first projection angle;
capturing a series of second projection image data sets containing second pixel values from a second projection angle, wherein the second projection angle is different from the first projection angle;
calculating a weighted average value for a respective voxel from pixel values of first- and second-pixels values of the projection beams that intersect in the respective voxel, wherein a confidence value of the first pixel value is used as a weight of the first pixel value and a confidence value of the second pixel value is used as a weight of the second pixel value to calculate the weighted average value, wherein the confidence values are determined as a function of a length of the vascular system that is traversed by a respective projection beam from a respective beam source through a respective pixel to the respective detector; and
producing the series of volume images using voxel values determined as a function of the weighted average values.

10. The method of claim 9, further comprising:
replacing a pixel value of a first pixel that includes a projection beam that intersects in a voxel with the projection beam of a second pixel by a second pixel value of the second pixel when the confidence value of the first pixel value falls below a first threshold value in order to determine a voxel value of the voxel and replacing a pixel value of the second pixel that includes a projection beam that intersects in the voxel with the projection beam of the first pixel by the first pixel value of the first pixel when the confidence value of the second pixel value falls below the first threshold value.

11. The method of claim 9, further comprising:
replacing a pixel value of a first pixel by a temporal interpolation, an interpolation, or the temporal interpolation and the interpolation between pixel values of pixels that are spatially adjacent to the first pixel when the confidence value of the first pixel value falls below a second threshold value in order to determine the voxel value of a voxel taking into account pixel values of first pixels and second pixels with projection beams that intersect in the voxel and replacing a pixel value of a second pixel by a temporal interpolation, an interpolation, or the temporal interpolation and the interpolation between pixel values of pixels that are spatially adjacent to the second pixel when the confidence value of the second pixel value falls below the second threshold value.

12. The method of claim 9, wherein capturing comprises:
capturing the series of first projection image data sets and the series of second projection image data sets at a constant first projection angle and a second projection angle; or
capturing the series of first projection image data sets and the series of second projection image data sets during a synchronous and rotation-angle-offset revolution or partial revolution of a first beam source-detector pair and a second beam source-detector pair in a common plane of rotation or during a synchronous and rotation-angle-offset revolution or partial revolution of the two beam source-detector pairs;
wherein a respective detector of the first beam source-detector pair and the second beam source-detector pair revolves in a plane of rotation that is spaced apart at a distance from the plane of rotation in which the beam source that is assigned to the respective detector revolves.

13. The method of claim 9, further comprising:
obtaining a first three-dimensional mask image from the first projection image data set and the second projection image data set of a synchronous and rotation-angle-offset revolution or partial revolution of a first beam source-detector pair and a second beam source-detector pair by removing, from the first projection image data set and the second projection image data set or the volume image data reconstructed therefrom, such data that changes during the revolution or partial revolution of the first beam source-detector pair and the second beam source-detector pair.

14. The method of claim 13, further comprising:
obtaining the series of volume images of the vascular system taking into account a second three-dimensional mask image from a mask run, a third three-dimensional mask image that is obtained from an external data source, or the second three-dimensional mask image and the third three-dimensional mask image.

15. The method of claim 9, wherein the second projection angle is offset by 90° from the first projection angle.

* * * * *